United States Patent [19]

Kinsey et al.

[11] Patent Number: 5,391,883
[45] Date of Patent: Feb. 21, 1995

[54] OZONE METER

[75] Inventors: James H. Kinsey, Baldwin, Md.; Richard J. Harms, Alexandria, Va.

[73] Assignee: Applied Research Corporation, Landover, Md.

[21] Appl. No.: 178,178

[22] Filed: Jan. 6, 1994

[51] Int. Cl.⁶ .......................................... G01N 21/33
[52] U.S. Cl. ..................................................... 250/372
[58] Field of Search ............ 250/372 R, 373, 372 EM

[56] References Cited

U.S. PATENT DOCUMENTS

| | | | |
|---|---|---|---|
| 3,896,313 | 7/1975 | Berman et al. | 250/372 |
| 4,652,761 | 3/1987 | Kerr et al. | 250/372 |
| 4,749,865 | 6/1988 | Scheller | 250/372 |
| 5,008,548 | 4/1991 | Gat | 250/372 |
| 5,036,311 | 7/1991 | Moran et al. | 250/372 |
| 5,107,123 | 4/1992 | Shi | 250/372 |
| 5,151,600 | 9/1992 | Black | 250/372 |

FOREIGN PATENT DOCUMENTS 1207640 8/1989 Japan.

OTHER PUBLICATIONS

Zurer, Pamela S. "Researchers Lack Data on Trends in UV Radiation at Earth's Surface" C & EN, (Jul. 26, 1993).

DeLuisi, John J. et al "A Determination of the Absolute Radiant Energy of a Robertson-Berger Meter Sunburn Unit" Atmospheric Environmental vol. 17, No. 4, pp. 751-758 (1983).

Frederick, John E. et al "The Budget of Biologically Active Ultraviolet Radiation in the Earth-Atmospheric System" Journal of Geophysical Research, vol. 93, pp. 3825-3832, Apr. 20, 1988.

Berger, Daniel S. "Fluctuations and Trends in Environmental UV Loads" Human Exposure to Ultraviolet Risks and Regulations Human Exposure to Ultraviolet Radiation: Risks and Regulations, pp. 213-221 1987.

Scotto, Joseph et al, "Biologically Effective Ultraviolet Radiation: Surface Measurements in the United States", 1974 to 1985, Science, vol. 239, pp. 762-764.

Komhyr, W. D., "Operations Handbook-Ozone Observations with a Dobson Spectrophotometer", NOAA Environmental Research Laboratories Air Resources Laboratory, Boulder, Colo. 80303, Jun., 1980.

Primary Examiner—Carolyn E. Fields

[57] ABSTRACT

A method for measuring total column ozone in the atmosphere and an instrument for implementing this method is disclosed. The ozone meter generally includes a first photodetector sensitive to UV-B only, a second photodetector sensitive to visible light only, a position-sensitive detector for measuring solar zenith angle and a microprocessor for normalizing the UV-B response relative to the visible response and applying one or more stored algorithms to the measured and normalized UV-B value and solar zenith angle to correlate total column ozone to a set of measured or modeled surface irradiances covering a wide range of solar zenith angles and total column ozone values.

16 Claims, 4 Drawing Sheets

OZONE METER

FIELD OF THE INVENTION

The present invention pertains to radiation measurement instruments and, more particularly, to instruments and a method for the measurement of total column ozone observed from a location on the surface of the earth.

DISCUSSION OF THE PRIOR ART

The spectrum of solar irradiance at the earth's surface is the result of attenuation of the radiation incident at the top of the atmosphere by the various components of the atmosphere. The ultraviolet through visible portion of the solar spectrum, ranging from about 280 to 700 nanometers (nm), incident at the earth's surface is attenuated primarily by four effects: Rayleigh scattering by air molecules, absorption by water vapor, scattering by dust, and absorption by ozone. Rayleigh scattering by air molecules is the largest contributor to attenuation between 320 and 620 nm. Dust scattering dominates for the remainder of the visible spectrum. Ozone absorption primarily affects the short wavelengths below about 340 nm with a very strong absorption feature centered near 250 nm such that solar radiation is reduced to a barely detectable level at 280 nm with rapidly decreasing attenuation up to about 320 nm where attenuation is dominated by Rayleigh scattering. Ultraviolet spectral radiation from about 280 to 320 nm, known as the UV-B band, is important from a biological point of view and is the component most directly affected by the total ozone. Concerns about ozone layer depletion reflect fears about the effects of increased UV-B radiation on plant and animal life, particularly potential carcinogenic effects and DNA disruption, and sweeping effects on overall weather and climate.

The connection between the ozone layer and the levels of UV-B in the biosphere was only discovered in the 1880's. In 1921 Fabry and Buisson were the first to accurately measure ozone concentrations, and five years later A.M.B. Dobson combined improving optics and electronics to produce a more-or-less portable meter capable of measuring ozone using a two wavelength attenuation technique developed by Fabry and Buisson.

Total ozone observations are made with the Dobson spectrophotometer by measuring the relative intensities of selected pairs of ultraviolet waves of different wavelengths emanating from the sun. The wave pair consists of a wave of first wavelength (or narrow band of wavelengths) that is highly absorbed by ozone, and a second that is relatively unaffected. Outside the earth's atmosphere the relative intensity of the two waves remains essentially fixed, but in passing through the atmosphere to the instrument both waves lose intensity equally due to scattering by air molecules and dust particles. The first wave, however, is strongly attenuated passing through the ozone layer whereas the second wave passes virtually intact. The relative intensity of the first wave compared to the second as seen by the instrument, therefore, varies with the amount of ozone present in the atmosphere. Thus, by measuring the relative intensities of pairs of waves with suitably selected wavelengths with the Dobson instrument, it is possible to determine how much ozone is present in the column of air extending from the instrument toward the sun. Total ozone is usually measured in Dobson Units (DU) and is the total amount of ozone in a vertical column from the surface to the top of the atmosphere compressed into a small column at Standard Temperature and Pressure (STP). The DU is defined such that 100 DU = 1 mm of Ozone. The UV absorption by ozone is a function of wavelength and the total amount of ozone in the intervening atmosphere. The Dobson spectrophotometer measures total ozone directly in DU only when the solar zenith angle is zero, otherwise it must be corrected for the geometric column depth, or actual atmospheric path length S, as a function of atmospheric thickness, h, the earth's radius, R, and the zenith angle, $\theta$, to wit:

$$S = -R\cos\theta + \sqrt{R^2\cos^2\theta + h^2 + 2Rh}$$

Dobson instrument measurements must be corrected by tabulated path lengths, computer-generated as a precise function of time and location for each instrument installation. In addition, the instruments are costly, heavy and complicated to calibrate, maintain and operate.

SUMMARY OF THE INVENTION

Accordingly, it is a primary object of the present invention to overcome the above-mentioned disadvantages of the prior art by providing an improved instrument and method for measuring the total ozone column from any location of the earth's surface.

Another object of the present invention is to simultaneously measure ozone concentrations and solar zenith angles.

Yet another object of the present invention is to provide an instrument and method for instantaneously measuring ozone column thickness at any location without the need for externally input geophysical constants.

Some of the advantages of the present invention over the prior art are that the ozone meter of the present invention is accurate, easy to operate, inexpensive to manufacture, portable, and self-contained.

The present invention is generally characterized by an ozone meter having at least one pair of photodiodes, one sensitive to radiation in a narrow wavelength band within the UV-B spectrum and the other sensitive to radiation in a narrow wavelength band near but outside the UV-B spectrum; a two-dimensional position-sensitive detector (PSD) is also provided. A microprocessor samples the signals from the two photodiodes, processes these signals into quotients representing UV-B intensity to non-UV-B intensity, and solves a polynomial regression equation using prestored calibration constants and the solar zenith angle simultaneously measured by the PSD to determine the column amount of ozone at any given time.

Other objects and advantages of the present invention will become apparent from the following description of the preferred embodiment taken in conjunction with the accompanying drawings.

DESCRIPTION OF THE PREFERRED EMBODIMENT

Figure 1:
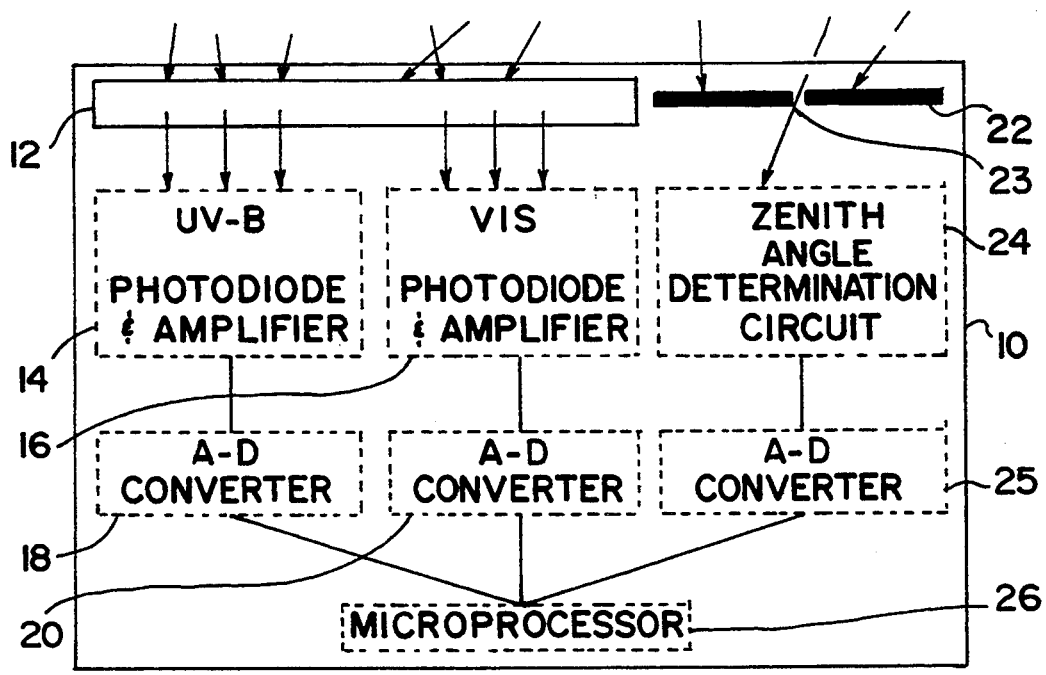
FIG. 1 is a block diagram of an ozone meter of the present invention.

Referring to FIG. 1, an ozone meter 10 according to the present invention includes a diffuser 12. A UV-B spectrum photodetector amplifier circuit 14 and a visible spectrum photodetector amplifier circuit 16 receive light energy from the diffuser and provide output signals to analog to digital (A–D) converters 18 and 20, respectively. An opaque plate 22 having a centered pinhole 23 passes light to a zenith angle determination circuit 24 feeding an analog to digital converter 25. A controller or microprocessor circuit 26 processes output signals from A–D converters 18, 20 and 25.

The diffuser 12 of, for instance, ground silica, provides an integrated Lambertian sum of the diffuse, or scattered, irradiance and the direct irradiance.

Figure 2:
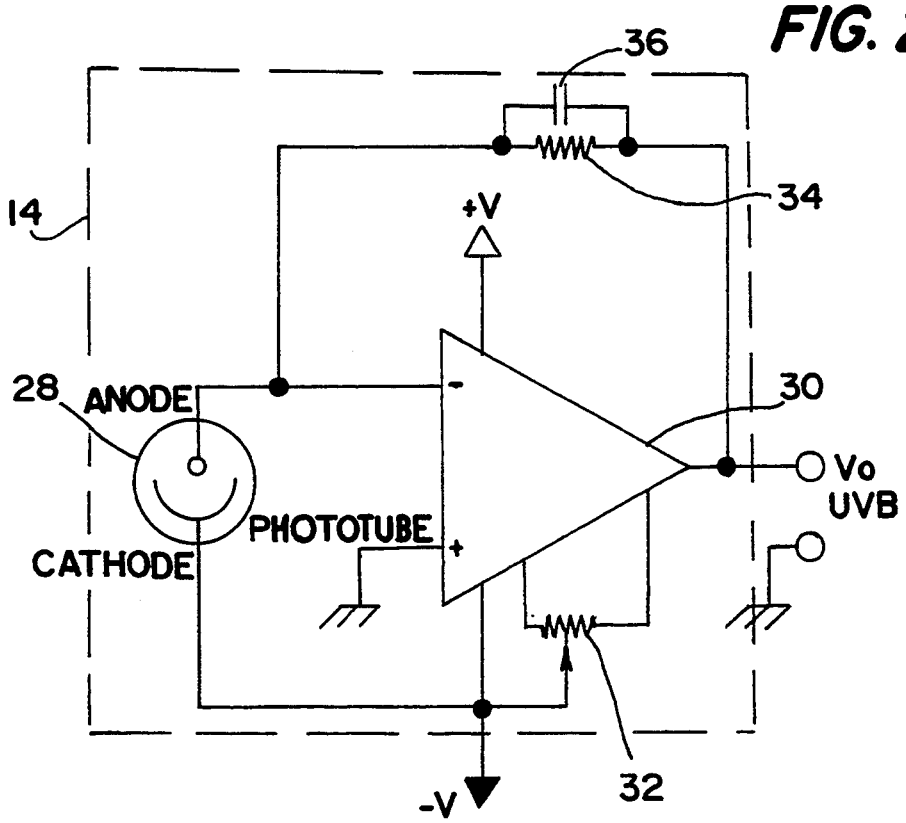
FIG. 2 is a schematic diagram of the UV-B spectrum photodetector amplifier circuit of the present invention.

The UV-B spectrum photodetector amplifier circuit 14, shown in detail in FIG. 2, includes a CsTe (cesium-telluride) photocathode phototube 28, for instance the Model R1826 sold by Hamamatsu Phonics of Hamamatsu City, Japan. Photodiode 28 is insensitive to wavelengths longer than about 320 nm and therefore requires no additional filtration. The UV-B photodiode output signal is amplified by an operational amplifier 30, such as the National Semiconductor LF441 JFET sold by National Semiconductor Corporation of Santa Clara, Calif. A balance variable resistor 32 of, for example, 25 K-ohms, is provided to adjust the DC offset of the amplified signal. A parallel combination of a gain adjusting feedback resistor 34 of, for example, 10 to 30 M-ohms, and a noise reduction capacitor 36 of, for example, 100 picofarads, is connected in negative feedback relation to amplifier 30.

Figure 3:
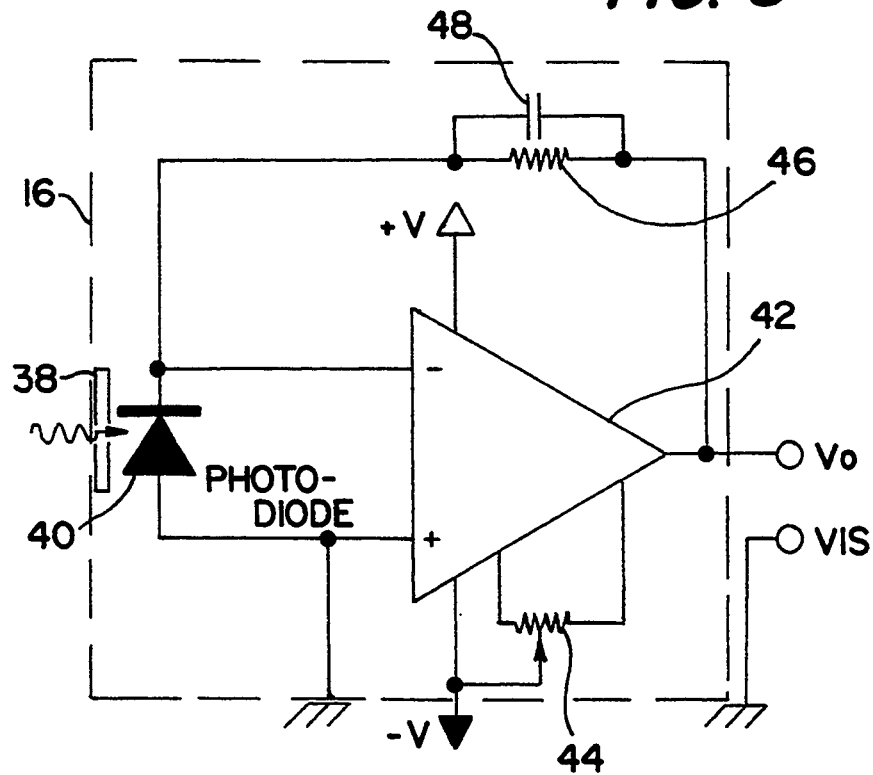
FIG. 3 is a schematic diagram of the visible spectrum photodetector amplifier circuit of the present invention.

The visible spectrum photodetector amplifier circuit 16 shown in FIG. 3 includes a short wavelength blocking filter 38, for example a layer of Schott GG-420 glass, to eliminate UV-B response. A semiconductor photodiode 40 is responsive to solar radiation in the visible range, preferably in a band at the lower end of the visible spectrum, and may be the Model G1962 GaP (gallium phosphide) photodiode marketed by Hamamatsu with a Schott GG-420 shortwave blocking filter. The photodiode output signal, responsive to non-UV-B irradiance, is amplified by a high impedance FET-input operational amplifier 42, such as the previously indicated LF441. A balance variable resistor 44 and a parallel combination of a feedback resistor 46 and a noise reduction capacitor 48 are provided and have values similar to those in the UV-B photodiode output circuit.

Figure 4:
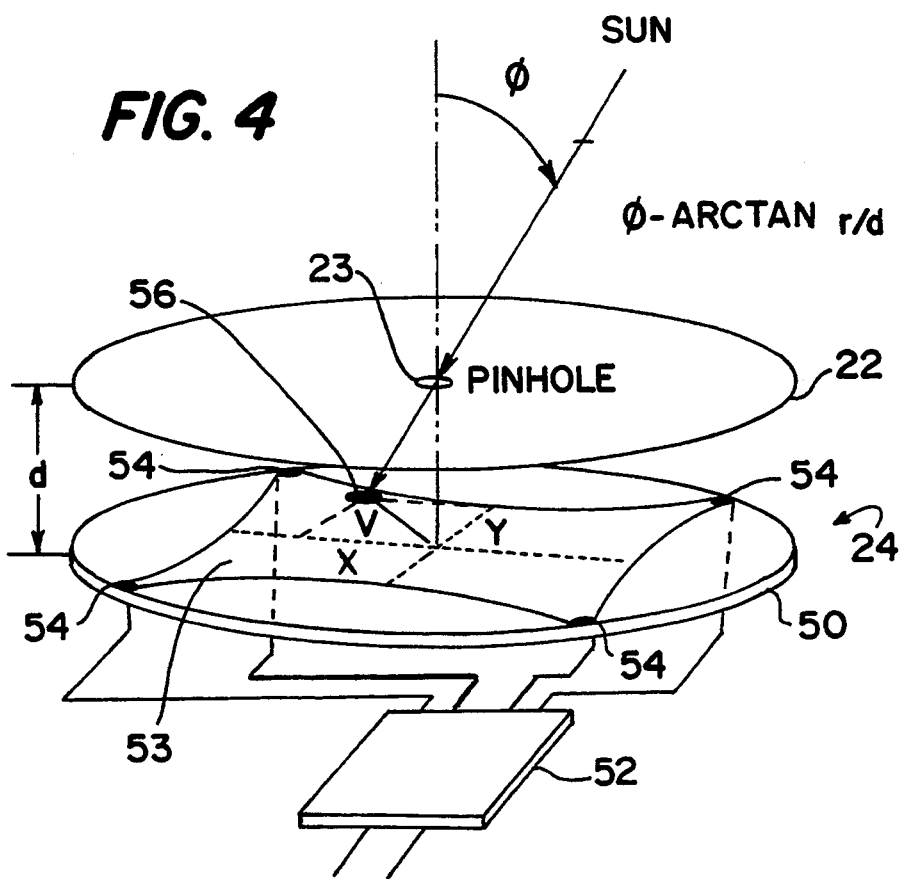
FIG. 4 is a schematic diagram of the two-dimensional position-sensitive detector (PSD) of the present invention.

The zenith angle determination circuit 24 shown in FIG. 4 includes a two-dimensional position-sensitive detector (PSD) 50 and supporting read-out printed circuit board 52, for instance the Hamamatsu Improved Tetra-Lateral Type No. 1880 silicon PSD described in the Hamamatsu Large-Area PSD Series Technical Data brochure. This device is a photosensitive detector combined with a uniformly resistive area 53 having four corner electrodes 54. A point of light 56 focused on the photosensitive surface produces a photocurrent at each electrode proportional to the distance from the point to the respective electrode. The supporting read-out printed circuit board 52 converts these four currents into two output voltages proportional to the x and y coordinates of the light point on the PSD.

The PSD is mounted in the ozone meter in the horizontal plane with an opaque plate 22 centered over and parallel to the PSD surface separated by a distance d. A pinhole 23 in opaque plate 22 is located directly over the center of PSD 50 and focuses solar radiation in the form of an image of the sun as a point of light 56 on the photosensitive surface. The coordinates of this image are represented by analog output signals from printed circuit board 52, are converted to digital form by A–D converter 25. The resulting digital signals are used to compute distance r shown in FIG. 4 in the following manner:

$$r = (x^2 + y^2)^{\frac{1}{2}}$$

where r is the radial distance from the center of the PSD to the solar image, and x and y are the coordinates of the solar image computed by printed circuit board 52. This distance r is proportional to the tangent of the solar zenith angle $\theta$ and is combined in microprocessor 26 with separation distance d to compute:

$$\theta = \arctan r/d = \arctan (x^2+y^2)^{\frac{1}{2}}/d.$$

The path length, S, through the atmosphere of direct rays of the sun are calculated as:

$$S = -R\cos\theta + \sqrt{R^2\cos^2\theta + h^2 + 2Rh}$$

where S is the path length, $\theta$ is the solar zenith angle as calculated above, R is the radius of the earth and h is the nominal thickness of the atmosphere.

The output signals from the UV-B and visible spectrum photodetector amplifier circuits 14 and 16, respectively, are weighted integrals of the response functions of the instruments to the incident solar irradience spectrum. These signals are converted from analog to digital form by converters 18 and 20 respectively (FIG. 1), and fed into the microprocessor 26 as digital data.

The microprocessor samples simultaneous values from the two input photodetector data signals and computes the quotient:

$$Q(\Omega,\theta) = U(\theta,\Omega)/V(\theta)$$

where $U(\theta,\Omega)$ is the UV-B detector output response signal modulated by ozone attenuation, and $V(\theta)$ is the ozone-independent visible light detector output, each associated with a corresponding solar zenith angle. The value of the quotient $U(\theta,\Omega)/V(\theta)$ can be set by adjustment of the relative gains of the UV-B and visible signal amplifiers or by a scaling constant.

A function:

$$f(\Omega,\theta) = \frac{e^{-\Omega/\Omega 0}}{S(\theta)/h}$$

where $\Omega$ is the total column ozone, $\Omega_0$ is a normalizing factor, $S(\theta)$ is the atmospheric path length and h is a nominal atmospheric thickness is plotted against the $U(\theta,\Omega)/V(\theta)$ quotient. The values of normalizing constants $\Omega_0$ and h are adjusted to optimize the distribution for linearity. A least squares curve fit of the resulting optimized distribution results in a slope-intercept equation:

$$\frac{e^{-\Omega/\Omega_0}}{S(\theta)/h} = Y_0 + m \frac{u(\theta,\Omega)}{v(\theta)}$$

which can be solved for $\Omega$ to yield:

$$\Omega = -\Omega_0 \left[ \ln(S(\theta)/h) + \ln\left(Y_0 + m \frac{U(\theta,\Omega)}{V(\theta)}\right) \right]$$

where $Y_0$ is the y-intercept of the curve fit, m is the line slope and $\Omega_0$ and h are defined as above. This equation, along with associated constants, is stored in the microprocessor 26 and solved using simultaneously sampled values of $U(\theta,\Omega)$, $V(\theta)$ and $\theta$, input signals from the UV-B and visible spectrum photodetector circuits and the solar zenith determination circuit 14, 16, and 24 respectively.

Figure 5:
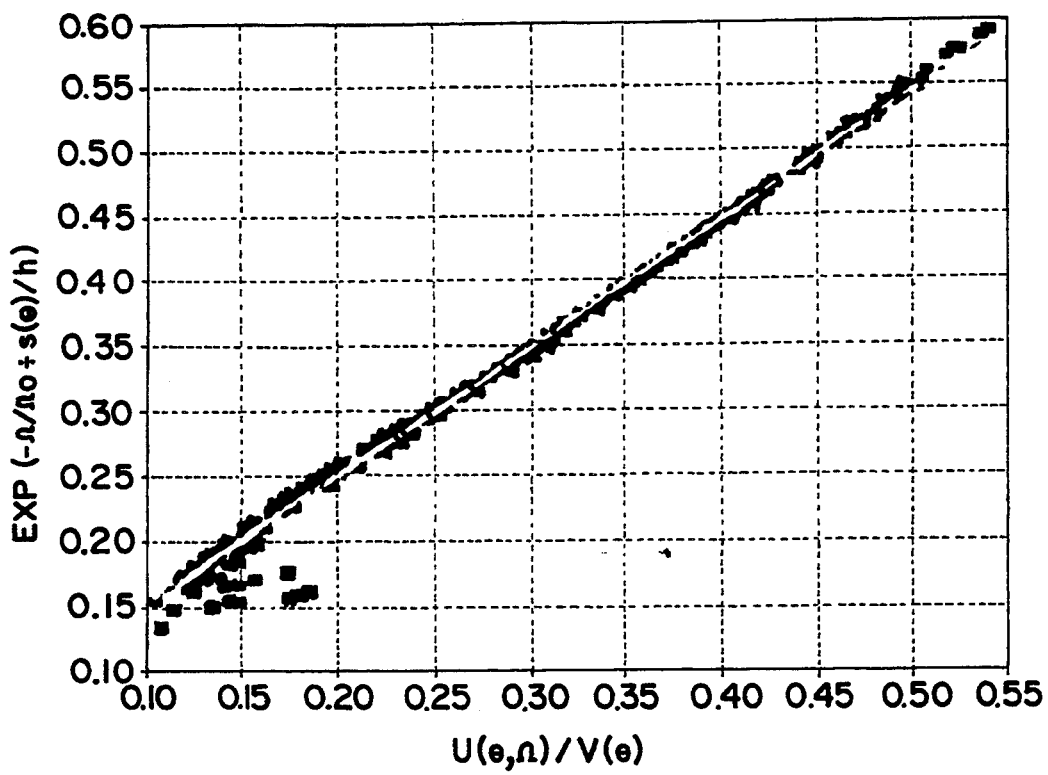
FIG. 5 is a plot of a function of total column ozone and zenith angle $(e^{-\Omega/\Omega o} \div S(\theta)/h)$ versus the weighted integral of the CsTe photodiode response to UV-B divided by a visible radiance $(E_{uv}(\Omega,\theta) \div E_{vis}(\Omega,\theta))$.

In an examplar embodiment the values used to represent the optimized function $f(\Omega,\theta)$ in the above discussion are produced by a model program described by J. E. Frederick and D. E. Lubin in a paper entitled "The Budget of Biologically Active Ultraviolet Radiation in the Earth-Atmosphere System" in the Journal of Geophysical Research, 93, 3825–3832, (1988) using values of $\Omega_0$ and h of 500 and $1.0 \times 10^8$ cm, respectively. A plot of the distribution is shown in FIG. 5. A least squares fit of this distribution produces a solution for $\Omega$ where the Y intercept $Y_o$ has a value of 0.525, and the slope m has a value of 0.983. Ideally, any comprehensive and representative set of real or modeled surface irradiances can be used to represent $f(\Omega,\theta)$, for instance values generated by the network of Dobson spectro-photometers established by the National Science Foundation.

It should be noted that the linearization of the data distribution discussed above is independent of $U(\Omega,\theta)/v(\theta)$. Calibration of the system is accomplished by using a broad-band light source, such as a 75 W high pressure Xenon lamp which emits from 200 nm up through the visible spectrum. A calibrated version of such a lamp can be used in the field to adjust the value of $U(\Omega,\theta)/v(\theta)$ to a standard value. This is the value originally used to obtain $Y_0$ and $\theta$, and permits extremely quick and uncomplicated field calibration of the ozone meter of the present invention by simply adjusting the gains of at least one of the photodetector circuits to re-achieve the initial quotient.

Figure 6:
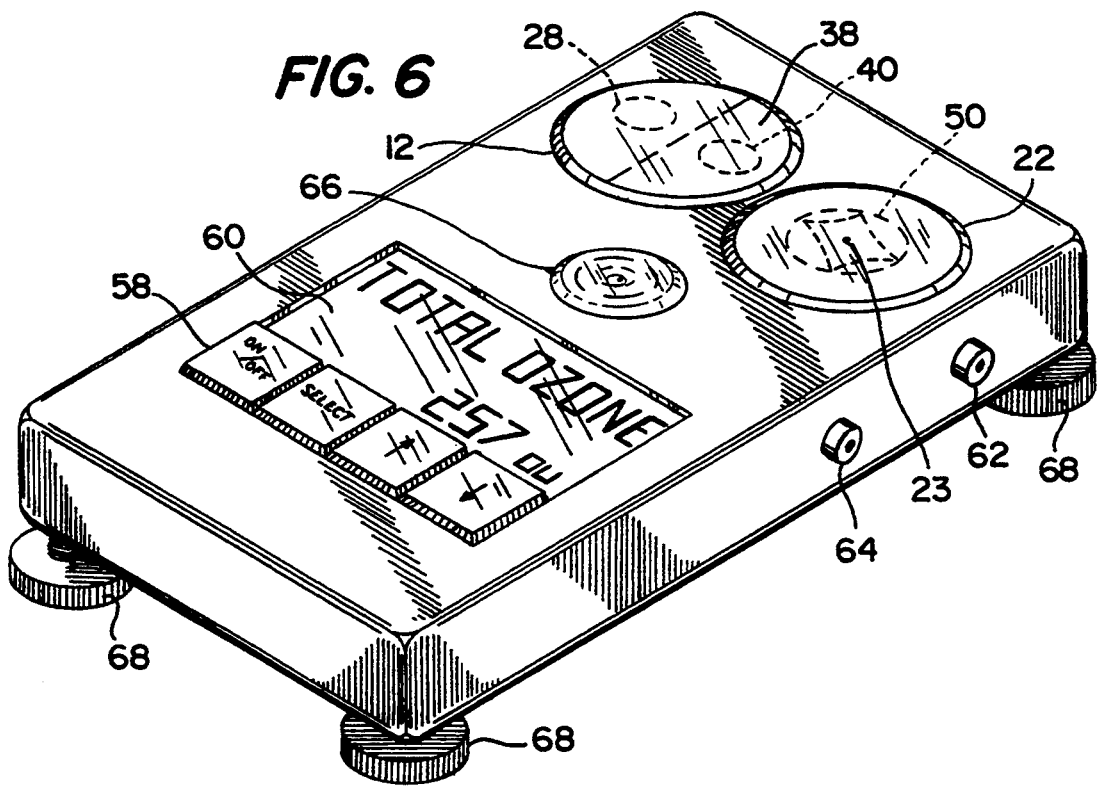
FIG. 6 is a perspective view of an ozone meter of the present invention.

Local control and display means are provided by, for example, a keypad 58 and LCD display panel 60, respectively, as shown in FIG. 6. A digital serial port 62 is provided to allow direct connection between the ozone meter and a computer, plotter, electronic storage unit or other such device. A connector 64 is provided for connection to an external electrical power source; alternatively the monitor can be energized by a battery. A diffuser 12 is shown on the face of the monitor with the unfiltered UV-B sensitive CsTe photodiode 28, the visible light sensitive GaP photodiode 40, and filter 38, shown in phantom therebehind. Opaque plate 22 with pinhole opening 23 is also shown with the PSD 50 in phantom therebehind. The monitor is designed for use in a horizontal position with the diffuser, photodiodes, opaque plate and PSD directed toward the zenith. A level indicating device 66 is mounted on a flat horizontal face of the meter, and selectively adjustable leveling mechanisms are included on at least one of the at least three support legs 68.

Figure 7:
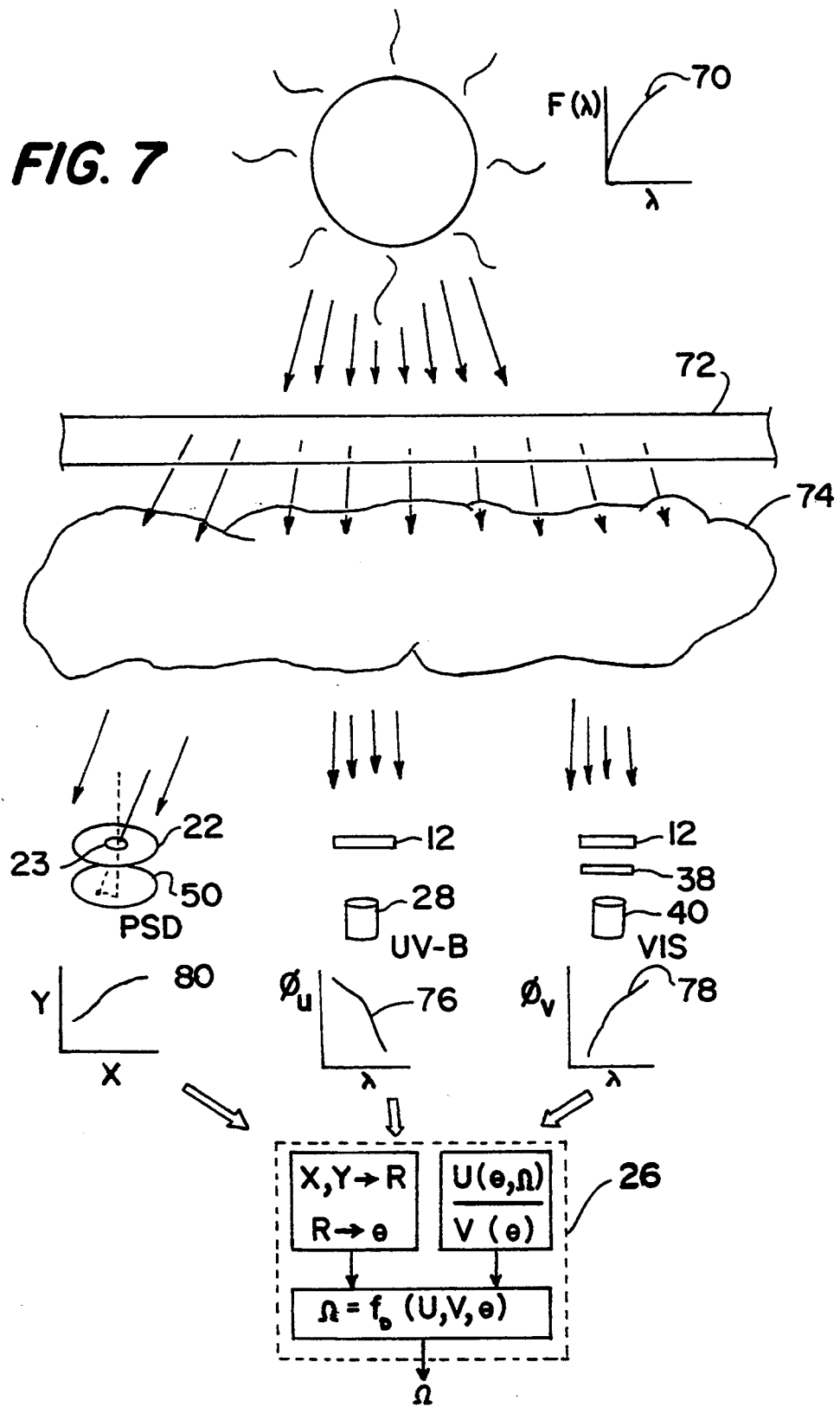
FIG. 7 is a diagram illustrating the operation of the ozone meter of the present invention in acquiring and processing atmospheric data.

In use the ozone meter of the present invention is leveled and energized, and solar radiation, represented in FIG. 7 by a spectrum plot 70 of energy as a function of wavelength, passes through, among other less influential attenuators, atmospheric ozone 72 and cloud cover 74 before passing through diffuser 12 to reach the UV-B photodiode 28. The energy also passes through diffuser 12 and short wavelength blocking filter 38 to reach visible spectrum photodiode 40 and through pinhole 23, centrally located with respect to PSD 50, in opaque plate 22 to reach PSD 50 of the ozone meter. Cloud cover 74 affects solar radiation evenly across the range of wavelengths, reducing the amplitude but not the shape of the solar spectrum. Atmospheric ozone 72, on the other hand, affects the UV-B wavelengths in an uneven, frequency-dependent manner but has negligible effect in the visible range. The interaction of the filtered incident solar radiation with the photodetectors produces response functions illustrated by the plots 76 and 78 for the UV-B and visible photodetectors, respectively. The beam of solar light focused as a point on the PSD 50 produces a response function describing the x and y coordinates of the light point as shown in plot 80. The photodetector responses are combined by the microprocessor to form the quotient of UV-B signal to visible range signal at any simultaneously determined solar zenith angle, and these values, along with input constants of calibration and correlation, are used to calculate total column ozone as described by a selected model or test data set representing surface solar irradiances, solar zenith angles and total column ozone. Values of total column ozone are displayed on the LCD display panel 60, or the processed signals can be transmitted directly to an externally located computer through port 62.

Total ozone measurements closely approximating those generated by expensive and intricate prior art instruments can be made at any location by the present invention. The compactness, simplicity of operation and ease of calibration will support the need for widespread and frequent atmospheric monitoring necessary to preserve and protect earth's resources.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An ozone meter for assessing total column ozone in the atmosphere comprising:
 a first photodetector amplifier circuit, including a first photodetector, responsive to solar radiation in the UV-B band for producing an output signal proportional to the weighted integral of incident UV-B solar radiation;
 a second photodetector amplifier circuit, including a second photodetector, responsive to solar radiation in the visible band for producing a second output signal proportional to the weighted integral of a portion of incident visible solar radiation;

a diffuser for integrating both diffuse and direct irradiance entering said first and second photodetectors;

a short wavelength blocking filter preventing UV-B radiation from entering said second photodetector amplifier circuit;

a horizontally mounted opaque plate having a centrally located pinhole passing therethrough;

a position sensitive detector circuit centrally located beneath said pinhole responsive to a point of sunlight focused through said pinhole onto a horizontal photosensitive surface for producing output currents proportional to the position coordinates of said point of light on said surface;

means for selectively adjusting said ozone meter to obtain horizontal alignment of said opaque plate and said position sensitive detector circuit;

a microprocessor for a) sampling values from said first and second output signals and creating a quotient by dividing said first UV-B signal by said second visible band signal; and b) sampling position coordinate values from said position sensitive detector circuit and calculating the corresponding solar zenith angle;

at least one algorithm stored in said microprocessor for determining total column ozone as a function of said quotient and the calculated solar zenith angle;

means for applying said at least one algorithm to said quotient and solar zenith angle to determine the magnitude of said total column ozone; and a display for reporting said total column ozone.

2. The ozone meter as recited in claim 1 further comprising at least one analog to digital converter for converting said first and second output signals from analog form to digital form.

3. The ozone meter as recited in claim 1 wherein said first UV-B photodetector amplifier circuit includes a CsTe photodiode.

4. The ozone meter as recited in claim 1 wherein said second visible band photodetector amplifier circuit includes a semiconductor GaP photodiode.

5. The ozone meter as recited in claim 1 wherein said diffuser has a Lambertian response.

6. The ozone meter as recited in claim 1 wherein said diffuser is ground silica.

7. The ozone meter as recited in claim 1 wherein said display is an LCD panel.

8. The ozone meter as recited in claim 1 wherein said position sensitive detector circuit includes a tetra-lateral silicon PSD.

9. The ozone meter as recited in claim 1 wherein said means for selectively adjusting horizontal alignment includes a level indication device affixed to a surface parallel to said photosensitive surface and at least one height-adjustable support mechanism.

10. The ozone meter as recited in claim 1 wherein said at least one algorithm is based on the solution to a curve fit of a comprehensive and representative distribution of surface irradiances defined as a function of total column ozone and solar zenith angle plotted against corresponding values of said quotient.

11. The ozone meter as recited in claim 10 wherein said function is of the form:

$$f(\Omega,\theta) = [e^{-\Omega/\Omega_0} \div (S(\theta)/h)]$$

where $f(\Omega,\theta)$ is ground level irradiance as a function of total column ozone and solar zenith angle, $\Omega$ is the total column ozone, $\Omega_0$ is a normalizing constant, $S(\theta)$ is the atmospheric path length of direct rays of the sun defined as:

$$S = -R\cos\theta + \sqrt{R^2\cos^2\theta + h^2 + 2Rh}$$

where R is the radius of the earth, $\theta$ is the solar zenith angle and h is a nominal thickness of the atmosphere.

12. The ozone meter as recited in claim 11 wherein said distribution is optimized for linearity by adjusting the values of normalizing constants $\Omega_0$ and h.

13. The ozone meter as recited in claim 12 wherein said algorithm has the form:

$$\Omega = -\Omega_0 \left[ \ln(S(\theta)/h) + \ln\left( Y_0 + m\frac{U(\theta,\Omega)}{v(\theta)} \right) \right]$$

where $Y_0$ is the y-intercept, m is the slope of the least squares fit of said optimized distribution $U(\theta,\Omega)$ is the UV-B signal, and $v(\theta)$ is the visible signal.

14. The ozone meter as recited in claim 1 comprising calibration means for adjusting the gain of at least one of said amplifier circuits in response to a known broad band lamp to regain the original value of said quotient.

15. An ozone meter for measuring characteristics of the total column ozone in the atmosphere comprising:

a first photodetector amplifier circuit responsive to solar radiation in the UV-B band for producing an output signal proportional to the weighted integral of incident UV-B solar radiation;

a second photodetector amplifier circuit responsive to solar radiation in the visible band for producing a second output signal proportional to the weighted integral of a portion of incident visible solar radiation;

a diffuser for integrating both diffuse and direct irradiance entering said first and second photodetector amplifier circuits;

a short wavelength blocking filter to prevent UV-B radiation from entering said second photodetector amplifier circuit;

a horizontally mounted opaque plate having a centrally located pinhole passing therethrough;

a position sensitive detector circuit centrally located beneath said pinhole responsive to a point of sunlight focused through said pinhole onto a horizontal photosensitive surface for producing output currents proportional to the position coordinates of said point of light;

means for selectively adjusting said ozone meter to obtain horizontal alignment of said opaque plate and said position sensitive detector circuit; and means for applying said output signals to an externally located computer for processing.

16. A method for assessing total column ozone in the atmosphere comprising the steps of:

(a) measuring incident UV-B irradiance using a first photodetector circuit responsive only to UV-B irradiance;

(b) measuring incident irradiance in a visible band using a second photodetector circuit unresponsive to UV-B irradiance;

(c) measuring the solar zenith angle using a horizontally mounted position-sensitive detector circuit responsive to direct sunlight focused through a pinhole in an opaque plate centrally mounted above said position sensitive detector circuit;

(d) mathematically normalizing the response of said first UV-B photodetector circuit by the response of said second visible photodetector circuit to produce a measure of UV-B irradiance corrected for wavelength independent factors including clouds and smoke; and (e) mathematically correlating the total column ozone as characterized by a set of modeled or measured surface irradiances each associated with related values of solar zenith angle and total column ozone with the measured normalized UV-B response and solar zenith angle.

* * * * *